(12) United States Patent
Biedermann et al.

(10) Patent No.: US 9,089,369 B2
(45) Date of Patent: Jul. 28, 2015

(54) ROD ASSEMBLY AND MODULAR ROD SYSTEM FOR SPINAL STABILIZATION

(75) Inventors: Lutz Biedermann, VS-Villingen (DE); Wilfried Matthis, Weisweil (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1277 days.

(21) Appl. No.: 12/249,855

(22) Filed: Oct. 10, 2008

(65) Prior Publication Data

US 2009/0163953 A1 Jun. 25, 2009

Related U.S. Application Data (60) Provisional application No. 60/979,198, filed on Oct. 11, 2007.

(30) Foreign Application Priority Data

Oct. 11, 2007 (EP) .................................... 07019940

(51) Int. Cl.
*A61B 17/70* (2006.01)

(52) U.S. Cl.
CPC ............ *A61B 17/7026* (2013.01); *A61B 17/705* (2013.01); *A61B 17/7004* (2013.01); *A61B 17/7028* (2013.01)

(58) Field of Classification Search
CPC ........... A61B 17/7031; A61B 17/7004; A61B 17/7032; A61B 17/7011

USPC ............ 606/60, 246, 251–260, 263, 264–278
See application file for complete search history.

(56) References Cited

U.S. PATENT DOCUMENTS

| 4,289,123 | A | 9/1981 | Dunn |
| 4,553,273 | A | 11/1985 | Wu |

(Continued)

FOREIGN PATENT DOCUMENTS

| EP | 1 810 624 A1 | 7/2007 |
| JP | 2007-195979 A | 7/2007 |

(Continued)

OTHER PUBLICATIONS

European Search Report for European Application No. 07019940.1, filed Oct. 11, 2007 in the name of Biedermann Motech GmbH, European Search Report dated Mar. 19, 2008 and mailed Apr. 3, 2008 (6 pgs.)

*Primary Examiner* — Eduardo C Robert
*Assistant Examiner* — Michelle C Eckman
(74) *Attorney, Agent, or Firm* — Christie, Parker & Hale, LLP (57) ABSTRACT

A rod assembly for spinal stabilization is provided comprising a flexible tubular element having a first end section and a second end section, an adapter connected to the second end section, the adapter having an engagement structure for connection to other rod portions or other rod assemblies of a spinal stabilization device, wherein at least a portion of the adapter extends into or onto the second end section, a longitudinal core extending through the tubular element, the core having a first end extending through at least a portion of the first end section and a second end extending into the portion of the adapter and being freely movable therein.

26 Claims, 7 Drawing Sheets

(56) References Cited

U.S. PATENT DOCUMENTS

| | | |
|---|---|---|
| 5,672,175 A | 9/1997 | Martin |
| 7,329,258 B2 | 2/2008 | Studer |
| 2004/0049190 A1 | 3/2004 | Biedermann et al. |
| 2005/0056979 A1* | 3/2005 | Studer et al. .................. 267/118 |
| 2005/0085815 A1* | 4/2005 | Harms et al. .................... 606/61 |
| 2005/0154390 A1* | 7/2005 | Biedermann et al. ........... 606/61 |
| 2005/0171543 A1 | 8/2005 | Timm et al. |
| 2005/0203513 A1* | 9/2005 | Jahng et al. ..................... 606/61 |
| 2005/0203514 A1 | 9/2005 | Jahng et al. |
| 2005/0203517 A1 | 9/2005 | Jahng et al. |
| 2005/0203519 A1 | 9/2005 | Harms et al. |
| 2005/0261685 A1 | 11/2005 | Fortin et al. |
| 2005/0277926 A1* | 12/2005 | Farris .............................. 606/61 |
| 2006/0036240 A1 | 2/2006 | Colleran et al. |
| 2006/0129147 A1* | 6/2006 | Biedermann et al. ........... 606/61 |
| 2006/0142758 A1 | 6/2006 | Petit |
| 2006/0142760 A1 | 6/2006 | McDonnell |
| 2006/0149238 A1* | 7/2006 | Sherman et al. ................ 606/61 |
| 2006/0189984 A1 | 8/2006 | Fallin et al. |
| 2006/0195093 A1 | 8/2006 | Jahng |
| 2006/0212033 A1 | 9/2006 | Rothman et al. |
| 2006/0223612 A1* | 10/2006 | Walker et al. ................... 463/16 |
| 2006/0229612 A1* | 10/2006 | Rothman et al. ................ 606/61 |
| 2006/0264935 A1 | 11/2006 | White |
| 2006/0264937 A1 | 11/2006 | White |
| 2006/0293657 A1* | 12/2006 | Hartmann ....................... 606/60 |
| 2007/0043356 A1* | 2/2007 | Timm et al. ..................... 606/61 |
| 2007/0049937 A1 | 3/2007 | Matthis et al. |
| 2007/0129729 A1* | 6/2007 | Petit et al. ....................... 606/61 |
| 2007/0161995 A1* | 7/2007 | Trautwein et al. .............. 606/61 |
| 2007/0203446 A1* | 8/2007 | Biedermann et al. ........... 604/11 |
| 2007/0233095 A1 | 10/2007 | Schlaepfer |
| 2007/0270814 A1* | 11/2007 | Lim et al. ........................ 606/61 |
| 2008/0033435 A1 | 2/2008 | Studer et al. |
| 2008/0045951 A1 | 2/2008 | Fanger et al. |
| 2008/0058812 A1 | 3/2008 | Zehnder |
| 2008/0154307 A1 | 6/2008 | Colleran et al. |
| 2008/0177317 A1 | 7/2008 | Jackson |
| 2008/0234743 A1* | 9/2008 | Marik ............................ 606/257 |
| 2008/0234746 A1 | 9/2008 | Jahng et al. |
| 2008/0300633 A1* | 12/2008 | Jackson ........................ 606/257 |
| 2008/0312693 A1* | 12/2008 | Trautwein et al. ............. 606/246 |
| 2009/0048631 A1* | 2/2009 | Bhatnagar et al. ............. 606/246 |
| 2009/0105759 A1* | 4/2009 | Gimbel et al. ................. 606/246 |

FOREIGN PATENT DOCUMENTS

| | | |
|---|---|---|
| JP | 2007-195979 A | 8/2007 |
| WO | WO 03/047442 A1 | 6/2003 |
| WO | WO 2005/094704 A1 | 10/2005 |

* cited by examiner

ROD ASSEMBLY AND MODULAR ROD SYSTEM FOR SPINAL STABILIZATION

RELATED APPLICATION(S)

The present application claims the benefit of U.S. Provisional Patent Application Ser. No. 60/979,198, filed Oct. 11, 2007, the contents of which are hereby incorporated by reference in their entirety, and claims priority from European Patent Application EP 07 019 940.1, filed Oct. 11, 2007, the contents of which are hereby incorporated by reference in their entirety.

BACKGROUND

The present application relates to a rod assembly for spinal stabilization.

WO 03/047442 A1 describes a damping element for use in spinal stabilization, the damping element has an outer spring, an inner spring and an adapter piece on either side of the outer and the inner spring. The inner spring abuts against the end of the adapters on both sides and is therefore not freely movable at one end.

US 2005/0085815 A1 describes a spinal stabilization rod comprising a core which is accommodated in a flexible tubular rod with tolerance in the axial direction.

US 2007/0049937 A1 describes a spinal stabilization rod which has a flexible tubular portion and a rigid end portion on either side of the flexible tubular portion and a core extending through the flexible portion and at least a part of the rigid end portions. The core can be fixed on one side and is freely movable on the other side.

US 2005/0154390 A1 describes a flexible element which has a core and two rod-like adapters being connectable to each end of the flexible element. The core does not extend into the adapter.

Figure 1:
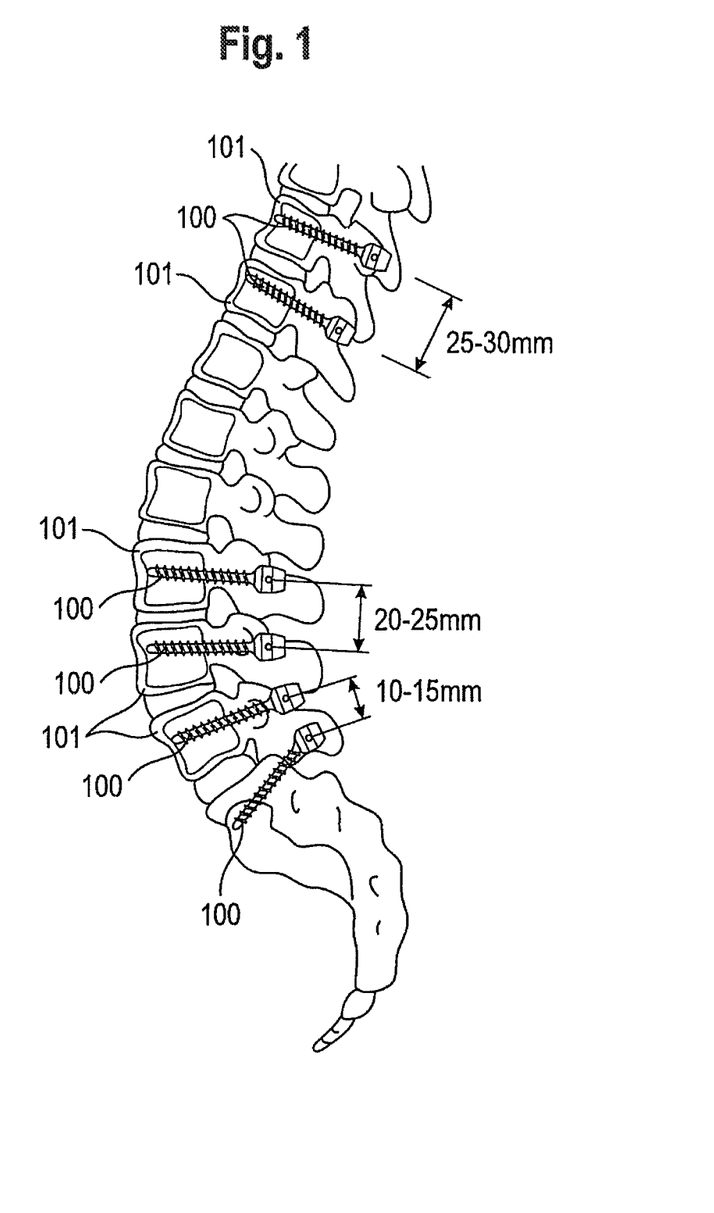
FIG. 1 shows a schematic view of the spinal column.

FIG. 1 shows a schematic representation of the spinal column together with bone anchoring elements 100 anchored, for example, in the pedicle of the vertebrae 101. Usually the bone anchoring elements are connected through a spinal stabilization rod which may be rigid (straight or curved) or flexible to some extent. As can be seen, the distance to be bridged by the rod between two bone anchoring elements is in the order of 25 to 30 mm in the higher thoracic region and decreases to 20 to 25 mm in the mid lumbar region until around 10 to 15 mm in the lower lumbar region. In specific clinical applications it may be necessary to stabilize different portions of the spine in a different manner, for example it may be necessary to use rigid as well as flexible stabilization at different locations. It may even be necessary to use a flexible stabilization with a different degree of flexibility at different locations of the spine, for example, on the right side and the left side. When considering the small distance between the bone anchoring elements in the lower lumbar part of the spine or in the cervical part of the spine, a compact shape and small dimensions of the stabilization rod or rod parts become necessary.

Based on the foregoing, there is a need to provide a rod assembly for spinal stabilization which can be used in a modular manner to allow a simple and versatile use, to provide a rod assembly which has small dimensions, and to provide a modular rod system for spinal stabilization.

SUMMARY OF THE INVENTION

According to aspects of the disclosure, a rod assembly for spinal stabilization includes a flexible tubular element and a core arranged within the flexible tubular element and an adapter on at least one side of the flexible tubular element. The adapter allows the tubular element to be connected to other rod portions or other rod assemblies of a spinal stabilization device. At least one end of the core is freely movable. It extends into a portion of the adapter which itself extends into the tubular element, thus providing a compact design. The invention further relates to a modular rod system for spinal stabilization.

The rod assembly can be preassembled in various combinations of flexible tubular elements which form the flexible rod part and adapters in order to connect it with other rod assemblies or with rigid rod parts. This modular design enables treatment of spinal disorders in a manner most adapted to the specific clinical requirements of a patient.

Due to the compact design it is possible to use the rod assembly in all regions of the spine, i.e. also in those regions where the bone anchoring elements used have a very small distance from each others, such as the lower lumbar region or the cervical region.

Further features and advantages of the invention will become apparent from the detailed description of embodiments in conjunction with the accompanying drawings

DETAILED DESCRIPTION OF THE INVENTION

As shown in FIGS. 2 to 5 the rod assembly according to a first embodiment includes a tubular element 2 having a first end section 2a and a second end section 2b opposite to the first end section. The inner diameter of the tubular element is in the embodiment shown constant from the first end section 2a to the second end section 2b. The outer diameter of the tubular element is smaller in the first and the second end section compared to the portion in between the end sections. The tubular element includes a flexible section which provides bending and compression elasticity to the tubular element.

Figure 2:
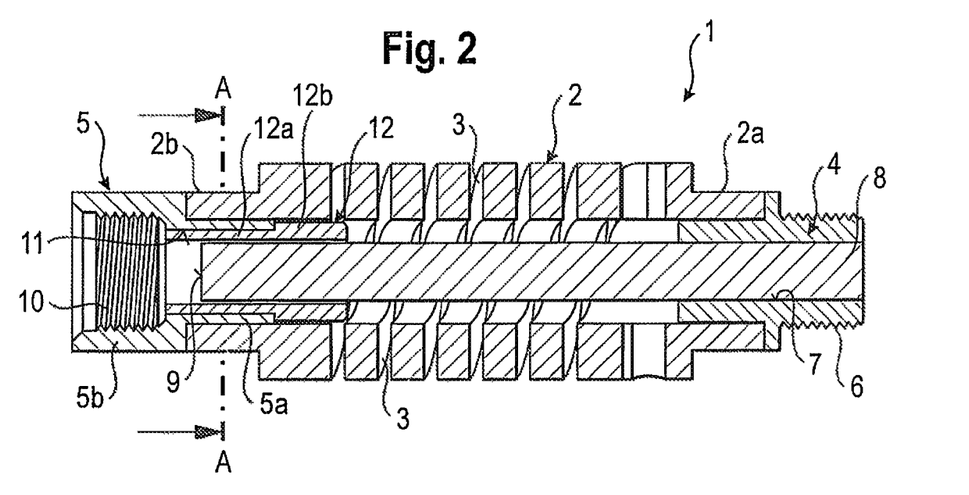
FIG. 2 shows a sectional view of the rod assembly along the rod axis.

Preferably, the flexible section is formed by a recess 3 extending in a helix-shaped manner over a length of the tubular element 2. The recess 3 imparts compression and bending elasticity to the tubular element 2. The dimension and pitch of the helix-shaped recess 3 as well as the wall thickness of the tubular element 2 is such that a desired elasticity is obtained. The recess 3 does not need to have a continuous helix shape, it can also be formed in a stepped manner including portions which are parallel to the longitudinal direction of the tubular element. The pitch of the helix can vary along the length.

Preferably, the tubular element is formed of a shape-memory alloy exhibiting a shape-memory effect and superelasticity. Particularly, the tubular element is made of a titanium-nickel alloy such as nitinol.

Figure 5:
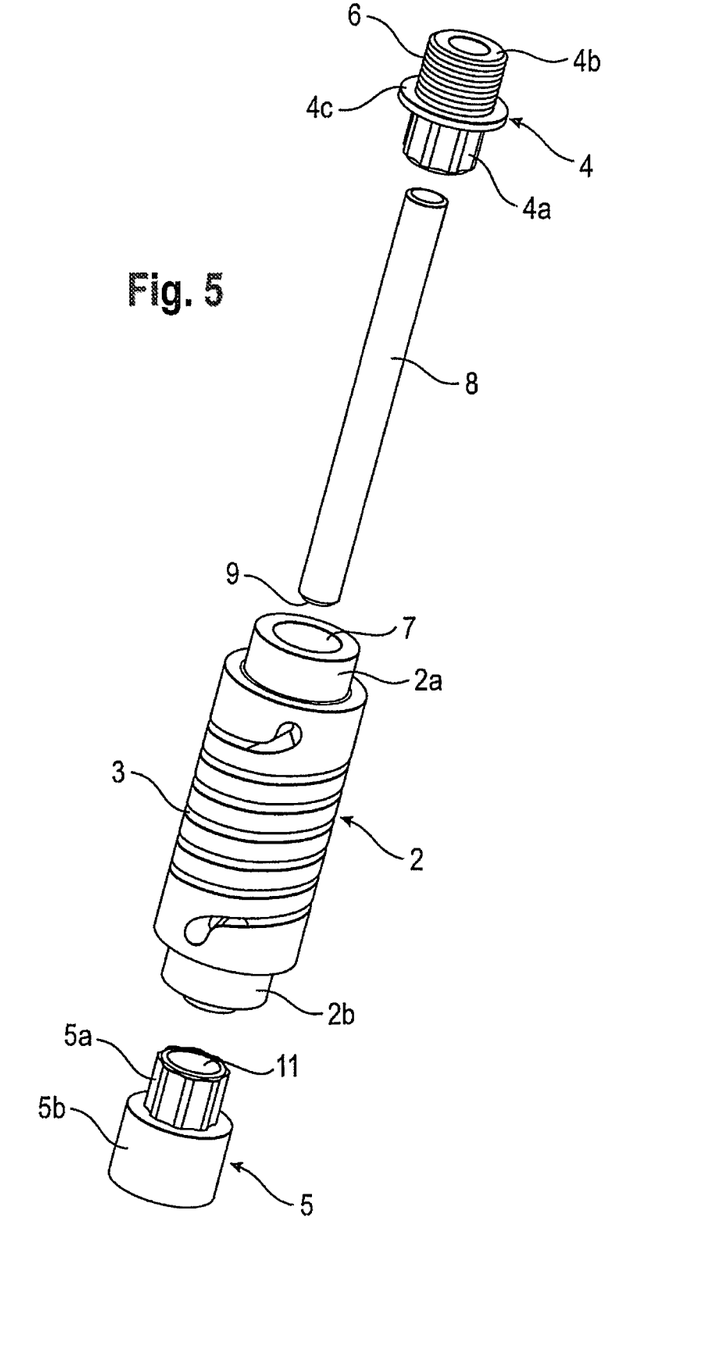
FIG. 5 shows a perspective exploded view of the rod assembly of FIG. 2.

The rod assembly further includes a first adapter 4 being connected to the first end section 2a and a second adapter 5 being connected to the second end section 2b. As shown in particular in FIGS. 2 and 5, the first adapter 4 includes a first section 4a which is connected to the first end section 2a of the tubular element 2 and second section 4b opposite to the first section 4a, a second section 4b serving for connection with further elements of a spinal stabilization device. The outer diameter of the first section 4a corresponds approximately to the inner diameter of the end section 2a of the tubular element 2. As shown in FIG. 5 the first section 4a of the first adapter has an outer surface with a polygon-shape, for example, with an octagon-shape. The second section 4b has an outer surface which is structured to be engaged with further elements. In the embodiment shown, the outer surface of the second section 4b has a thread 6. The first section 4a and the second section 4b are divided from each other by an annular shoulder 4c, the outer diameter of which corresponds to the outer diameter of the first end section 2a. The first adapter 4 further comprises a coaxial bore 7 extending through it from its first end to its second end.

The first adapter 4 is preferably made of a biocompatible metal, such as for example titanium. In the assembled state, the first adapter 4 is connected to the first end section 2a of the tubular element by means of a press-fit connection. The polygon-shape of the outer surface of the first section 4a of the first adapter leads to a connection which is a combination of a form-locking or positive-fit connection and a frictional connection. The type of the octagon is selected according to the desired strength of the connection. In particular, if the tubular element has nitinol, the press-fit connection can be established when the tubular element is in a cooled state, where the material is mainly in the martensitic state. In the martensitic state it is more easily deformable than in the austenitic state. Therefore, the polygon shape of the adapter can create a positive-fit connection in that it deforms the inner wall of the end section of the tubular element. Also, in the martensitic state the forces for assembly are reduced.

The rod assembly 1 further includes a core 8 which has in the embodiment shown a cylindrical shape and a diameter which is such that it can be connected by means of a press-fit connection to the first adapter 4. The core 8 is thus fixedly connected to the first adapter 4 and therefore to the first end section 2a of the tubular element 2. It extends from the end of the first adapter 4 to approximately the end of the second end section 2b. Hence, it extends fully through the elastic section of the tubular element 2. The length of the core 8 is such that in a fully compressed state of the tubular element 2 the free end should not abut against the second adapter 5. The free end 9 of the core is not fixed and is therefore freely movable within the tubular element 2. The core 8 is preferably made of a shape-memory alloy, such as titanium nickel alloy, for example of nitinol. Particularly, it can be a nitinol wire.

The second adapter 5 has, as can be seen in FIGS. 2 and 5, a first section 5a and a second section 5b. The first section 5a has an outer diameter which approximately corresponds to the inner diameter of the second end section 2b of the tubular element and has in this embodiment a polygon-shape. The second section 5b has an outer diameter which corresponds to the outer diameter of the second section 2b of the tubular element. The second section 5b includes a structure for engagement with further elements of a bone stabilization device. In the embodiment shown, it includes a threaded bore 10 for connection with a threaded rod part or adapter. The second adapter 5 further includes a coaxial bore 11 extending from the free end of the first section 5a to the bottom of the threaded bore 10. The inner diameter of the coaxial bore 11 is larger than the outer diameter of the core 8. When the second adapter 5 is connected to the tubular element 2 the core 8 extends through a portion of the bore 11.

The second adapter 5 is made of a biocompatible material, for example of titanium.

Figure 3A:
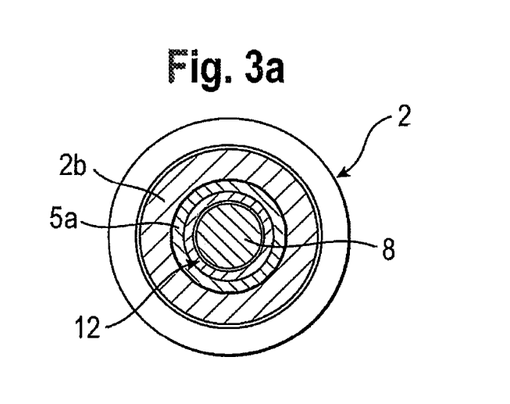
FIG. 3a shows a sectional view of the rod assembly along the line A-A shown in FIG. 2.
Figure 3B:
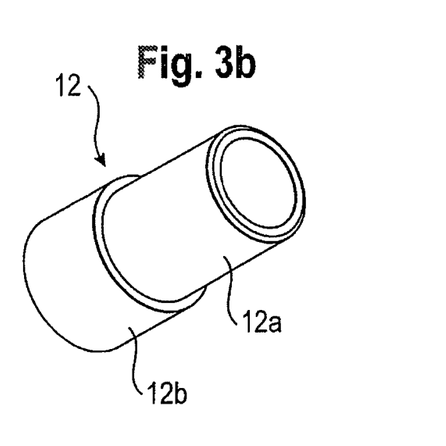
FIG. 3b shows a perspective view of an element of the rod assembly according to FIG. 1.
Figure 4:
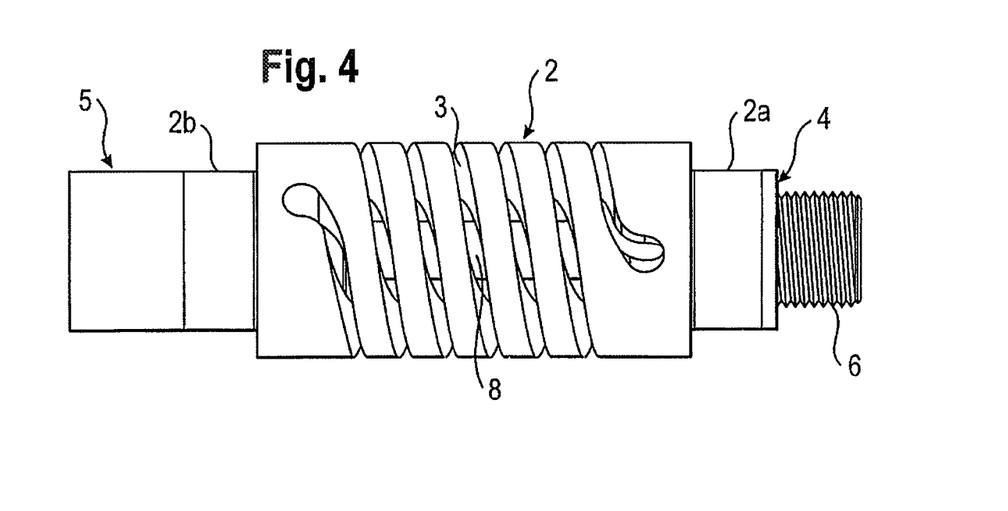
FIG. 4 shows a side view of the rod assembly of FIG. 2.

As can be seen in particular in FIGS. 2 and 3b, a bushing 12 is arranged between the first portion 5a of the second adapter and the core 8. The bushing 12 has first portion 12a which is connected by means of a press-fit connection to the first section 5a of the second adapter. Accordingly, the outer diameter of the bushing 12 in the first portion 12a is approximately the same as the inner diameter of the coaxial bore 11. The end of the first portion 12a abuts to the end of the bore 11. The second portion 12b has a diameter which is slightly smaller than the inner diameter of the tubular element. The inner diameter of the bushing is slightly larger than the outer diameter of the core 8, so that the core 8 can slide within the bushing. The length of the bushing is such that during flexion, the core does not slide out of the bushing. The bushing is made of a material which facilitates sliding of the core 8. For example, it can be made of polyetheretherketone (PEEK), carbon fiber reinforced polyetheretherketone (CRF PEEK), polytetrafluoroethylene (PTFE) or other biocompatible materials suitable for bearings. Biocompatible coatings for improved bearing properties may also be used.

The core 8 serves for stiffening the elastic tubular element. For example, without the core 8, the tubular element 2 may undergo kinking in certain load conditions. The core 8 prevents such kinking.

The dimensions materials and properties of the elements of the rod assembly are selected such that a specific rod assembly has specific desired characteristics as far as the elasticity and the design of the adapters are concerned.

Since the core 8 should be freely movable on one side, it is necessary to provide the space for the movement of the core. By arranging the movable end of the core in at least a part of the second adapter the overall length of the rod assembly can be reduced. Also, the length of the flexible part of the rod assembly can be reduced. This makes it possible to use the rod assembly, for example, in the lower lumbar part of the spine.

Figure 6:
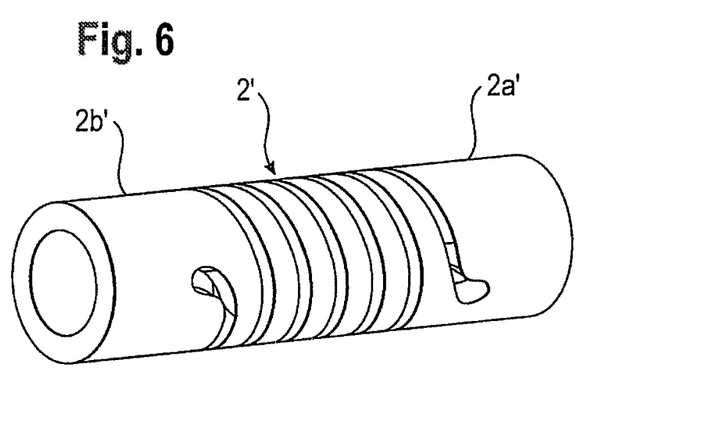
FIG. 6 shows a second embodiment of the tubular element of the rod assembly.

Various modifications of the embodiment described are possible. FIG. 6 shows a second embodiment wherein the tubular element 2' has end sections 2a' and 2b' with an outer diameter which is the same as that of the flexible section. For example, the tubular element 2' can have an outer diameter of 5.5 mm, whereas the tubular element 2 of the first embodiment can have an outer diameter of 7.5 mm for the flexible section and an outer diameter of 5 mm for the end sections.

Figure 7A:
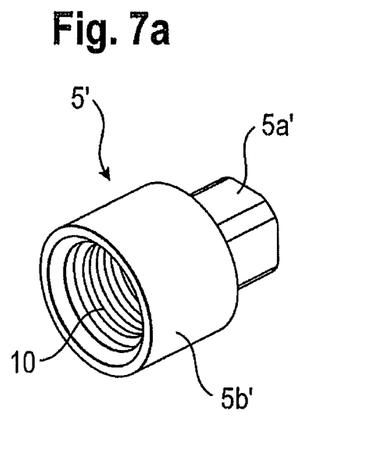
FIG. 7a to 7c show modifications of the adapter to be used with the tubular element according to FIG. 6.
Figure 7B:
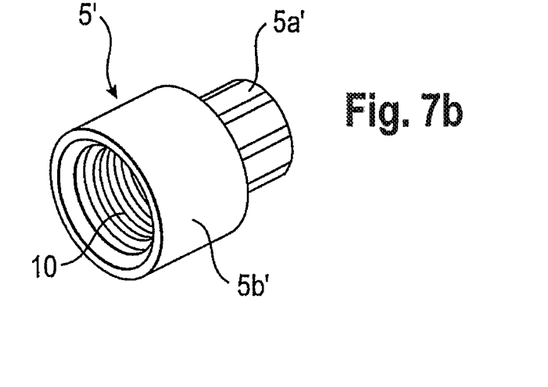
Figure 7C:
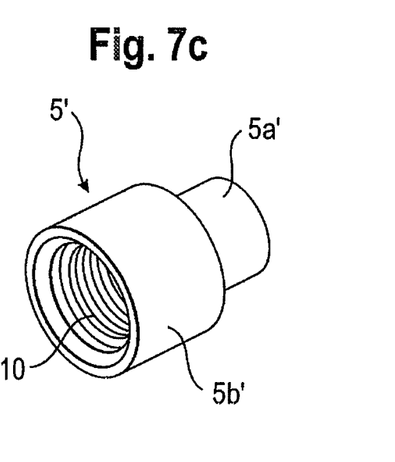

FIG. 7a to FIG. 7c show various modifications of the adapters. The adapters 5' are of the type of the second adapter 5. The same parts are designated with the same reference numerals. The adapters 5' comprise a threaded bore 10 for connection with further parts of the bone stabilization device. The first section 5a' of the adapters can be shaped in various manners. FIG. 7a shows a quadrangular outer surface with flat edges, FIG. 7b shows an octagonal outer surface and FIG. 7c a cylindrical outer surface. The shape of the outer surface of the first section is selected such that the desired strength of the connection is achieved by a combination of a form-fit (or positive-fit) and frictional-fit connection. The outer diameter of the second section 5b' corresponds to the outer diameter of the second section 2b' of the tubular element.

Figure 8:
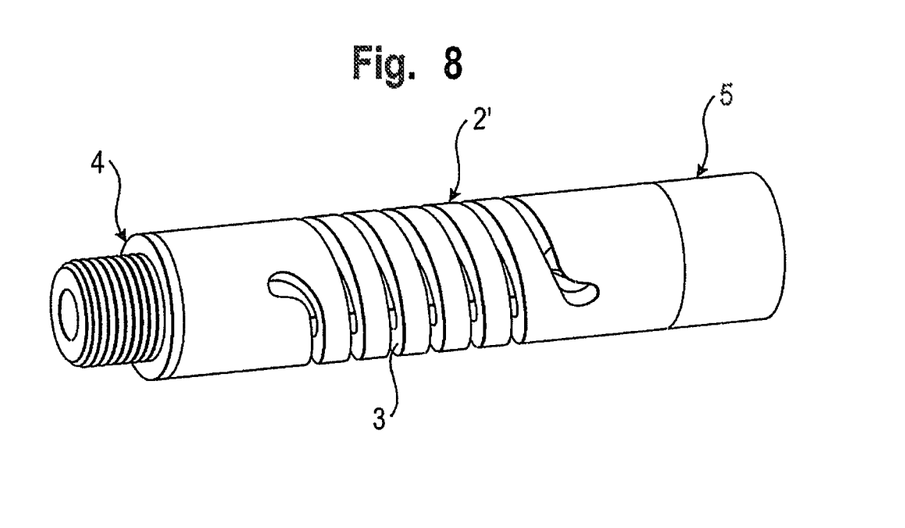
FIG. 8 shows a third embodiment of the rod assembly.

FIG. 8 shows the tubular element 2' of FIG. 6 with an adapter on either side. The adapter 5' corresponds to one of the adapters shown in FIG. 7a to FIG. 7c and the adapter 4 corresponds to the adapter shown in FIGS. 2 to 5.

Figure 9:
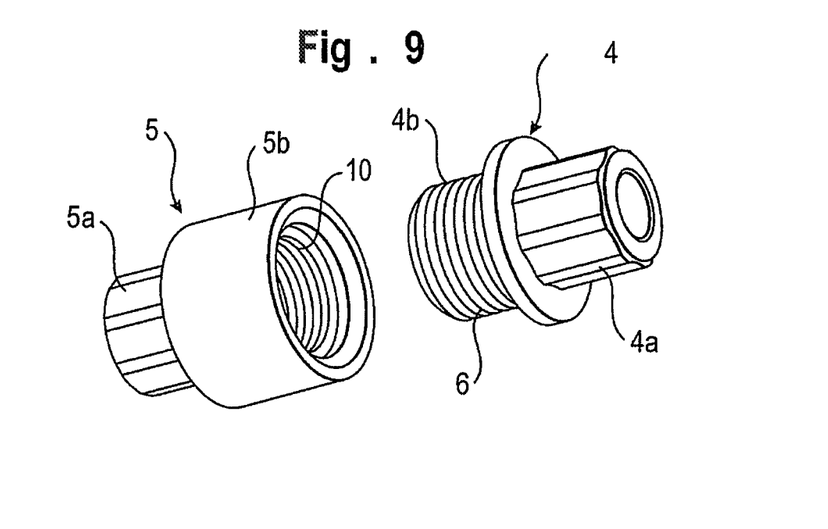
FIG. 9 shows a perspective view of two adapters to be used with the rod assembly of FIG. 8.

FIG. 9 shows an adapter of the type like the adapter 5, 5' and an adapter of the type like the adapter 4. As can be seen in FIG. 9 the outer thread 6 of the adapter 4 can engage with the inner thread of the threaded bore 10 of the adapter 5. This allows several rod assemblies to be combined in a bone stabilization device. In particular, it can provide a spinal stabilization rod of a certain length which has different sections with different flexible properties corresponding to the flexible properties of the respective rod assemblies.

Figure 10A:
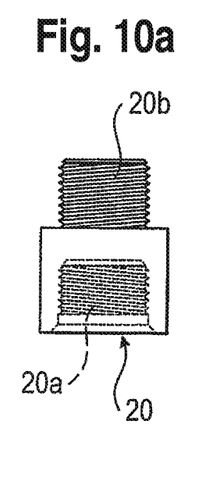
FIG. 10a to 10d show various embodiments of rigid rod adapters to be used with a rod assembly according to the invention.
Figure 10B:
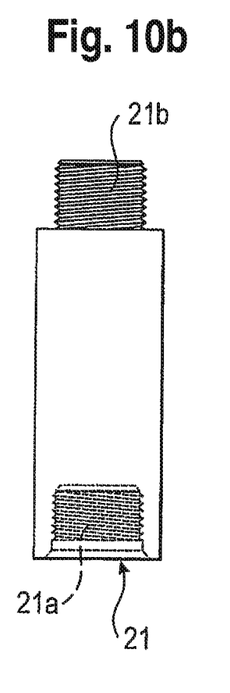
Figures 10C, 10D:
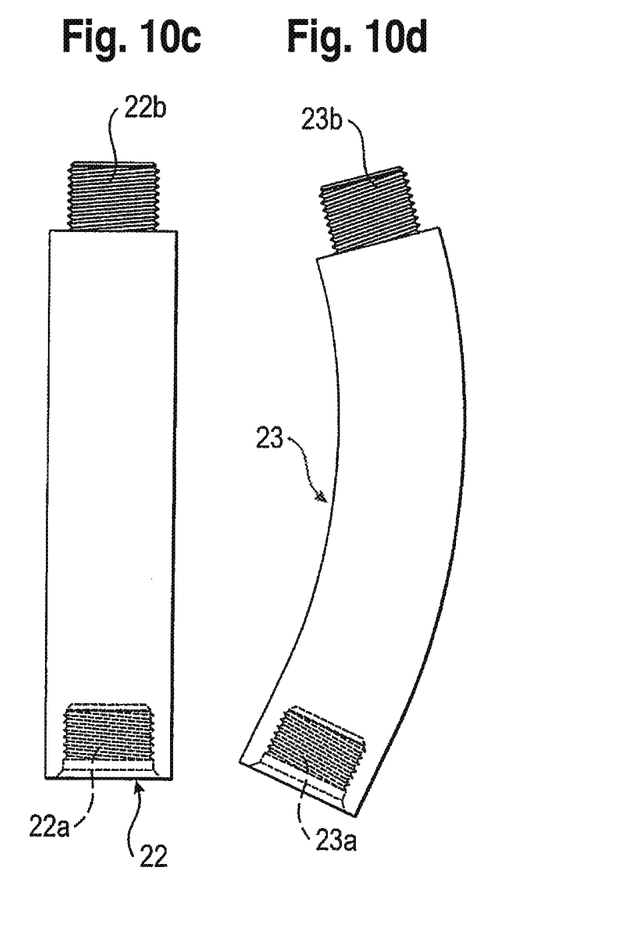

FIGS. 10a to 10d show various rigid rod portions 20,21,22 and 23 each having a threaded bore 20a,21a,22a and 23a on one end and a threaded projection 20b,21b,22b and 23b on the opposite end. The rigid rod portions can have different length as shown in FIGS. 10a to 10c or can have a curvature as shown in FIG. 10d. The threaded bore 20a to 23a engages with the thread 6 of the first adapter of the rod assembly and the threaded projection 20b to 23b engages with the threaded bore 10 of the second adapter 5. The rigid rod portions are made of a biocompatible material, for example of titanium or stainless steel.

Figure 11A:
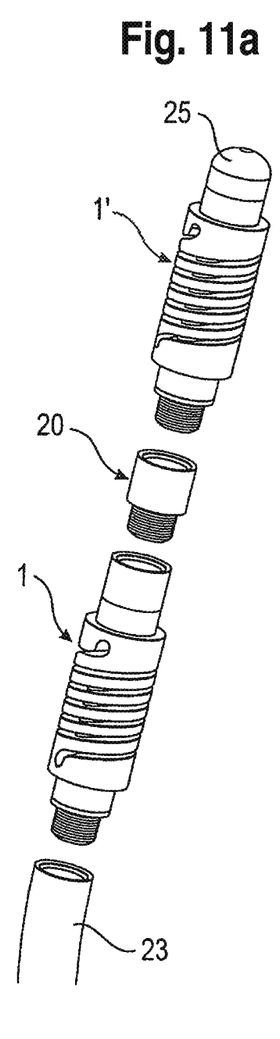
FIG. 11a to 11c show various combinations of rod assemblies and adapters.
Figure 11B:
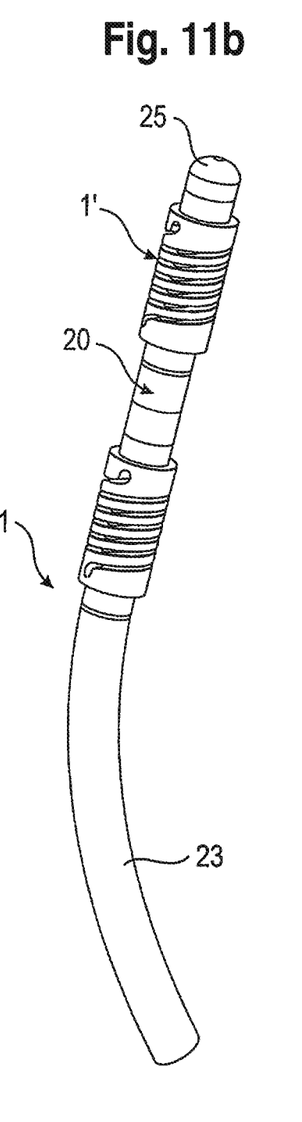
Figure 11C:
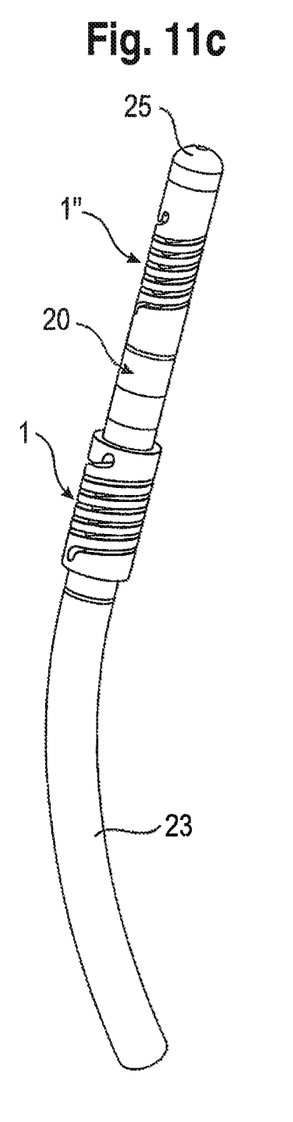

FIGS. 11a to 11c show examples of different spinal stabilization rods which are composed of several elements described herein. FIG. 11a shows a spinal stabilization device before it is assembled which includes a rigid rod portion 23, a rod assembly 1 of a specific length and specific elasticity, a further rigid rod portion 20 and a second rod assembly 1' which may have different characteristics than the first rod assembly 1. At the end of the stabilization device a rounded cap 25 is provided which engages with the end of the rod assembly. Of course, other designs of end caps are possible. FIG. 11b shows the bone stabilization device of FIG. 11a in an assembled state. FIG. 11c shows a similar bone stabilization device as that shown in FIGS. 11a and 11b. The only difference is that instead of the second rod assembly 1' a rod assembly 1" is used which has a smaller outer diameter than the first rod assembly 1 so that it is flush with the surface of the rigid rod section 20.

Further modifications are possible. Instead of threaded connections between the rod assembly and rigid rod portions other connections such as press-fit connections can be used. In a further modification the adapter has a portion which extends onto the end section of the tubular element and is fixed thereto, for example, by means of a press-fit connection. The various elements of the different embodiments can be combined with each other.

The core 8 can have a non-circular cross section, for example a rectangular cross section, to provide an enhanced stiffness in an oriented manner. Furthermore, the core 8 can be made of other materials than of a shape-memory alloy. For example, it can be made of biocompatible plastic material.

In use a set of rod assemblies of various outer diameters, various elastic or flexible properties, various lengths and various means for connection is provided. Further, a set of adapters of different types and of rigid rod portions of different length and/or curvatures is provided. The rod assembly, the adapters and the rigid rod portions form a modular rod system. The surgeon can select from this modular system the suitable elements to combine them to a spinal stabilization rod which can be connected to bone anchoring elements as shown in FIG. 1. In particular, different anatomical situations, for example on the left side or on the right side of the spine or in different regions of the spine can be taken into account by selecting and combining the suitable elements for correction.

What is claimed is:

1. A rod assembly for spinal stabilization comprising:
a flexible tubular element having a first end section, a second end section, and a flexible section between the first and second end sections, at least one of the first and second end sections having an annular shape in a cross-sectional plane perpendicular to a longitudinal axis of the flexible tubular element, the flexible tubular element being compressible from an uncompressed state to a fully compressed state;
an adapter having a first end that is connectable to the second end section and a second end having a threaded engagement surface that is configured to engage and connect to a corresponding threaded engagement surface of a connectable element of a spinal stabilization device;
wherein at least a portion of the first end of the adapter extends into or onto the second end section of the flexible tubular element when the adapter is connected to the second end section; and
a longitudinal core extendable through the flexible tubular element, the core having a first end extendable through at least a portion of the first end section of the flexible tubular element, and a second end extendable into the portion of the adapter that extends into or onto the second end section of the flexible tubular element;
wherein an end point at the second end of the core located furthest from the first end of the core along a longitudinal axis of the core is spaced apart from the adapter, such that the second end of the core is freely movable relative to the adapter along the longitudinal axis of the core when the adapter is connected to the second end section and the flexible tubular element is in the fully compressed state.

2. The rod assembly of claim 1, wherein the adapter is tubular and comprises a coaxial bore extending entirely through the adapter from the first end to the second end.

3. The rod assembly of claim 2, wherein the portion of the first end of the adapter has an outer cylindrical or polygon-shaped surface configured to engage and directly connect to the second end section of the flexible tubular element.

4. The rod assembly of claim 2, further comprising a first adapter connectable to the first end section, and wherein the adapter being connectable to the second end section is a second adapter.

5. The rod assembly of claim 4, wherein the first adapter has a first end that is connectable to the first end section of the flexible tubular element and a second end and comprises a tubular portion extending into the first end section of the flexible tubular element.

6. The rod assembly of claim 5, wherein the tubular portion of the first adapter has a cylindrical or polygon-shaped surface configured to engage and directly connect to the first end section of the flexible tubular element.

7. The rod assembly of claim 4, wherein at least one of the first adapter and the second adapter is connectable to the flexible tubular element with a press-fit connection.

8. The rod assembly of claim 4, wherein the core is configured to be fixed to the first adapter with a press-fit connection.

9. The rod assembly of claim 1, further comprising a bushing configured to be arranged inside the flexible tubular element and located radially between the adapter and the second end of the core to facilitate the sliding of the second end of the core.

10. The rod assembly of claim 9, wherein the bushing comprises polyetheretherketone (PEEK) or carbon fiber reinforced polyetheretherketone (CFR PEEK).

11. The rod assembly of claim 1, wherein the core is made of a shape-memory alloy.

12. The rod assembly of claim 1, wherein the flexible tubular element is made of a shape-memory alley.

13. The rod assembly of claim 1, wherein the flexible section of the flexible tubular element has a recess in its wall to provide elasticity.

14. The rod assembly of claim 1, wherein the core, at the first end, has a cross-sectional shape in a cross-sectional plane perpendicular to the longitudinal axis of the core having a closed outer perimeter surrounding the longitudinal axis of the core.

15. The rod assembly of claim 14, wherein the first end of the core is connected to the first end section of the flexible tubular element by a press-fit connection.

16. A rod assembly for spinal stabilization comprising:
a flexible tubular element having a first end section and a second end section;
an adapter having a first end that is connectable to the second end section and a second end having a threaded engagement surface that is configured to engage and connect to a corresponding threaded engagement surface of a connectable element of a spinal stabilization device;
wherein at least a portion of the first end of the adapter extends into or onto the second end section of the flexible tubular element when the adapter is connected to the second end section; and
a longitudinal core extendable through the flexible tubular element, the core having first end extendable through at least a portion of the first end section of the flexible tubular element, and a second end extendable into the portion of the adapter that extends into or onto the second end section of the flexible tubular element;
wherein an end point at the second end of the core located furthest from the first end of the core along a longitudinal axis of the core is spaced apart from the adapter, such that the second end of the core is freely movable relative to the adapter alone the longitudinal axis when the adapter is connected to the second end section, and
wherein the first end of the core is fixed to the first end section of the flexible tubular element.

17. A rod system for spinal stabilization comprising:
a rod assembly comprising:
a flexible tubular element having a first end section, a second end section, and a flexible section between the first and second end sections, at least one of the first and second end sections having an annular shape in a cross-sectional plane perpendicular to a longitudinal axis of the flexible tubular element, the flexible tubular element being compressible from an uncompressed state to fully compressed state;
an adapter having a first end that is connectable to the second end section and a second end having an engagement surface, wherein at least a portion of the first end of the adapter extends into or onto the second end section when the adapter is connected to the second end section; and
a longitudinal core extendable through the flexible tubular element, the core having a first end extendable through at least a portion of the first end section and a second end extendable into the portion of the adapter and being freely movable in the portion of the adapter along a longitudinal axis of the core when the adapter is connected to the second end section and the flexible tubular element is in the fully compressed state; and
a connectable element having an engagement surface at one end thereof, the engagement surface of the connectable element configured to threadably or press-fit engage and connect to the engagement surface of the adapter; and
wherein when the connectable element is connected to the adapter, an outer width of the connectable element at the connection is less than or equal to an outer width of the adapter at the connection, and the connectable element extends past the adapter and primarily away from the flexible tubular element in a direction along a longitudinal axis of the flexible tubular element.

18. The rod system of claim 17, wherein the connectable element is a rigid rod.

19. The rod system of claim 17, wherein the engagement surfaces of the adapter and the connectable element are threaded surfaces.

20. The rod system of claim 17, wherein the connectable element an end cap.

21. The rod system of claim 17, wherein the connectable element is a flexible rod.

22. The rod system of claim 17, wherein the adapter is tubular and comprises a coaxial bore extending entirely through the adapter from the first end to the second end.

23. A rod assembly for spinal stabilization comprising:
a flexible tubular element having a first end section, a second end section, and a flexible section between the first and end sections, at least one of the first and second end sections having an annular shape in a cross-sectional plane perpendicular to a longitudinal axis of the flexible tubular element, the flexible tubular element being compressible from an uncompressed state to a fully compressed state;
a first adapter connectable to the first end section, the first adapter comprising a first portion that extends into or onto the first end section and a second portion;
as second adapter connectable to the second end section, the second adapter comprising a first portion that extends into or onto the second end section and a second portion; and
a longitudinal core extendable through the flexible tabular element, the core having a first end extendable into the first adapter, a second end extendable into the second adapter and being freely movable in the second adapter along a longitudinal axis of the core when the second adapter is connected to the second end section and the flexible tubular element is in the fully compressed state; and
wherein the first adapter and the second adapter are configured to connect to each other by the second portion of one of the adapters being inserted into the second portion of the other one of the adapters.

24. A method of assembling a rod system for spinal stabilization, the rod system comprising:
a flexible tubular element having a first end section, a second end section, and a flexible section between the first and second end sections, at least one of the first and second end sections having an annular shape in a cross-sectional plane perpendicular to a longitudinal axis of the flexible tubular element, the flexible tubular element being compressible from an uncompressed state to a fully compressed state;

an adapter having a first end that is connectable to the second end section and a second end having an engagement surface, wherein at least a portion of the first end of the adapter extends into or onto the second end section when the adapter is connected to the second end section;

a longitudinal core extendable through the flexible tubular element, the core having a first end extendable through at least a portion of the first end section and a second end extendable into the portion of the adapter and being freely movable in the portion of the adapter along a longitudinal axis of the core when the adapter is connected to the second end section and the flexible tubular element is in the fully compressed state; and a connectable element having an engagement surface at one end thereof the engagement surface of the connectable element configured to engage and connect to the engagement surface of the adapter; and wherein when the connectable element is connected to the adapter, an outer width of the connectable element at the connection is less than or equal to an outer width of the adapter at the connection, and the connectable element extends past the adapter and primarily away from the flexible tubular element in a direction along a longitudinal axis of the flexible tubular element;

the method comprising:

connecting the adapter to the second end section of the flexible tubular element; and connecting the connectable element to the adapter by threadably or press-fit engaging the engagement surface of the connectable element with the engagement surface of the adapter.

25. The method of claim 24, further comprising inserting the core in the flexible tubular element.

26. A rod system for spinal stabilization comprising:

a first rod assembly comprising:

a first flexible tubular element having a first end section, a second end section, and a flexible section between the first and second end sections, at least one of the first and second end sections having an annular shape in a cross-sectional plane perpendicular to a longitudinal axis of the first flexible tubular element, the first flexible tubular element being compressible from an uncompressed state to a fully compressed state;

a first adapter connectable to the second end section of the first flexible tubular element, wherein at least a portion of the first adapter extends into or onto the second end section of the first flexible tubular element when connected to the second end section of the first flexible tubular element; and a first longitudinal core extendable through the first flexible tubular element, the first core having a first end extendable through at least a portion of the first end section of the first flexible tubular element and a second end extendable into the portion of the first adapter and being freely movable in the portion of the first adapter along a longitudinal axis of the first core when the first adapter is connected to the second end section of the first flexible tubular element and the first flexible tubular element is in the fully compressed state;

a second rod assembly comprising:

a second flexible tubular element having a first end section and a second end section; and a second adapter connectable to the first end section of the second flexible tubular element, wherein at least a portion of the second adapter extends into or onto the first end section of the second flexible tubular element when connected to the first end section of the second flexible tubular element; and a rod having a first end connectable to the first adapter and a second end connectable to the second adapter to connect the rod between the first flexible tubular element and the second flexible tubular element;

wherein for at least one of the first adapter or the second adapter, when the rod is connected to the one of the adapters, an outer width of the rod at the connection is less than or equal to an outer width of the one of the adapters at the connection.

\* \* \* \* \*

UNITED STATES PATENT AND TRADEMARK OFFICE
CERTIFICATE OF CORRECTION

PATENT NO. : 9,089,369 B2  
APPLICATION NO. : 12/249855  
DATED : July 28, 2015  
INVENTOR(S) : Lutz Biedermann et al.

Page 1 of 1

It is certified that error appears in the above-identified patent and that said Letters Patent is hereby corrected as shown below:

In the Claims

| | |
|---|---|
| Column 7, Claim 12, line 10 | Delete "alley." <br> Insert -- alloy. -- |
| Column 7, Claim 16, line 36 | After "having" <br> Insert -- a -- |
| Column 7, Claim 16, line 45 | Delete "alone" <br> Insert -- along -- |
| Column 7, Claim 17, line 58 | After "to" <br> Insert -- a -- |
| Column 8, Claim 20, line 24 | After "element" <br> Insert -- is -- |
| Column 8, Claim 23, line 33 | Before "end" <br> Insert -- second -- |
| Column 8, Claim 23, line 42 | Delete "as" <br> Insert -- a -- |
| Column 8, Claim 23, line 46 | Delete "tabular" <br> Insert -- tubular -- |

Signed and Sealed this  
Twenty-sixth Day of April, 2016

Michelle K. Lee  
*Director of the United States Patent and Trademark Office*